(12) United States Patent
Udell

(10) Patent No.: US 7,887,852 B2
(45) Date of Patent: Feb. 15, 2011

(54) SOFT GEL CAPSULES CONTAINING POLYMETHOXYLATED FLAVONES AND PALM OIL TOCOTRIENOLS

(75) Inventor: Ronald G. Udell, Beverly Hills, CA (US)

(73) Assignee: Soft Gel Technologies, Inc., Los Angeles, CA (US)

( * ) Notice: Subject to any disclaimer, the term of this patent is extended or adjusted under 35 U.S.C. 154(b) by 0 days.

(21) Appl. No.: 11/176,593

(22) Filed: Jul. 7, 2005

(65) Prior Publication Data
US 2006/0003947 A1 Jan. 5, 2006

Related U.S. Application Data

(63) Continuation-in-part of application No. 11/145,563, filed on Jun. 3, 2005.

(51) Int. Cl.
*A61K 36/00* (2006.01)
*A61K 9/00* (2006.01)
*A61K 47/00* (2006.01)
*A61K 9/48* (2006.01)

(52) U.S. Cl. ................ 424/725; 424/451; 424/400; 424/439

(58) Field of Classification Search .......... 424/725
See application file for complete search history.

(56) References Cited

U.S. PATENT DOCUMENTS

| | | | |
|---|---|---|---|
| 4,343,816 A | 8/1982 | Cavazza | |
| 4,599,232 A | 7/1986 | Bertelli | |
| 4,687,782 A | 8/1987 | Brantman | |
| 5,030,458 A | 7/1991 | Shug et al. | |
| 5,030,657 A | 7/1991 | Burtle et al. | |
| 5,240,961 A | 8/1993 | Shug | |
| 5,362,753 A | 11/1994 | Blum et al. | |
| 5,391,550 A | 2/1995 | Carniglia et al. | |
| 5,431,916 A * | 7/1995 | White ................ | 424/451 |
| 5,504,072 A | 4/1996 | Schmidl et al. | |
| 5,560,928 A | 10/1996 | DeFelice | |
| 6,239,114 B1 | 5/2001 | Guthrie et al. | |
| 6,251,400 B1 | 6/2001 | Guthrie et al. | |
| 6,436,431 B1 * | 8/2002 | Hoffpauer et al. ........ | 424/439 |
| 6,616,942 B1 | 9/2003 | Udel | |
| 6,623,734 B2 | 9/2003 | Udell et al. | |
| 6,683,104 B1 * | 1/2004 | Zhang ................ | 514/380 |
| 6,982,251 B2 * | 1/2006 | Ghosal et al. ............ | 514/23 |
| 6,987,125 B1 * | 1/2006 | Guthrie et al. ........... | 514/456 |
| 7,241,800 B2 * | 7/2007 | Huang ................ | 514/419 |
| 2002/0018772 A1 | 2/2002 | Udell et al. | |
| 2002/0094996 A1 * | 7/2002 | Rath ................ | 514/356 |
| 2002/0177585 A1 * | 11/2002 | Hofmann et al. ......... | 514/185 |
| 2004/0022876 A1 * | 2/2004 | Green et al. ............. | 424/736 |
| 2004/0152641 A1 | 8/2004 | Guthrie et al. | |
| 2004/0214882 A1 * | 10/2004 | Guthrie et al. ........... | 514/456 |
| 2005/0070611 A1 * | 3/2005 | Fantuzzi ............... | 514/690 |
| 2005/0249803 A1 | 11/2005 | Udell | |
| 2006/0083700 A1 * | 4/2006 | Cherukuri et al. ......... | 424/59 |

FOREIGN PATENT DOCUMENTS

| | | |
|---|---|---|
| WO | WO 01/70029 | 5/1988 |
| WO | WO 88/03015 | 5/1988 |
| WO | WO 99/15167 A | 4/1999 |

OTHER PUBLICATIONS

Dw ACC 2000-673500, Oct. 2000, Derwent, Elstener et al.*
DW ACC 2004-466295, Jan. 2004, Derwent, Novikov et al.*
S. C. Whitman et al., Atherosclerosis Jul. 26, 2004, Nobiletin, a citrus flavonoid isolated from tangerines, selectivity inhibits class A scavenger receptor-mediated metabolism of acetylated LDL by mouse macrophages, pp. 8.
General Principles, Goodman and Gilman's The Pharmaceutical Basis of Therapeutics, Chapter. 1, pp. 1-32, last edition Pagamonon Press.
Kirk-Othmer Encyclopedia Chemical Technology, Mark, et al., eds., 22:709-762 3d Ed (1983).
Soft Gel Technologies, Inc.: "Sytrinol? : Healthy Cholesterol Levels Naturally", 2004, http://www.soft-gel.com/prod/media/Sytrinol/Sytrinol_bro.pdf>.
Kurowaska, Elzbieta M. et al., "Cardioprotective effects of supplementation with citrus phytochemicals and tocotrienols in subjects with moderate hypercholesterolemia", FASEB Journal, vol. 18, No. 4-5, 2004, pp. Abst. 576.1.
Office Action (Restriction Requirement) dated Jul. 29, 2008, U.S. Appl. No. 11/145,563, 11 pages.
Amendment and Response to Restriction Requirement dated Oct. 29, 2008, U.S. Appl. No. 11/145,563, 10 pages.
Office Action dated Nov. 25, 2008, U.S. Appl. No. 11/145,563, 13 pages.
Amendment and Response to Office Action dated Apr. 27, 2009, U.S. Appl. No. 11/145,563, 14 pages.

(Continued)

*Primary Examiner*—Christopher R Tate
*Assistant Examiner*—Randall Winston
(74) *Attorney, Agent, or Firm*—Dorsey & Whitney LLP

(57) ABSTRACT

The present invention is directed to soft gel compositions, methods of delivery and packaged nutraceuticals of the soft gel compositions that include at least one polymethoxylated flavone and, optionally, at least one tocotrienol. Optional active ingredients include a phytosterol, DHA, EPA, coenzyme Q-10 or an analog thereof and mixtures thereof.

18 Claims, 6 Drawing Sheets

OTHER PUBLICATIONS

Final Office Action dated Jul. 2, 2009, U.S. Appl. No. 11/145,563, 11 pages.
Request for Continued Examination and Amendment and Response to Final Office Action dated Dec. 2, 2009, U.S. Appl. No. 145,563, 10 pages.
Declaration Pursuant to 37 C.F.R. § 1.132 of Ronald G. Udell dated Nov. 30, 2009, U.S. Appl. No. 11/145,563, 30 pages.
Office Action dated Dec. 28, 2009, U.S. Appl. No. 11/145,563, 10 pages.
Amendment and Response to Office Action dated Jun. 28, 2010, U.S. Appl. No. 11/145,563, 12 pages.
Declaration Under 37 C.F.R. 1.131 filed Jun. 28, 2010, U.S. Appl. No. 11/145,563, 4 pages.
Office Action dated Oct. 15, 2010, U.S. Appl. No. 11/145,563, 21 pages.

* cited by examiner

Figure 1. Baseline characteristics of subjects in Sytrinol™ pharmacokinetics study (mean ± SD)

| Parameter | Mean ± SD |
|---|---|
| Females | 5 |
| Males | 5 |
| Age | 23 ± 3 |
| Heart Rate | 70 ± 4 |
| Systolic blood pressure (mm Hg) | 125 ± 10 |
| Diastolic Blood pressure (mm Hg) | 82 ± 8 |
| Weight (Kg) | 76.5 ± 17.9 |
| Height (m) | 1.75 ± 0.08 |
| BMI (kg/m$^2$) | 24.68 ± 4.13 |
| Glucose (mmol/L) | 4.7 ± 0.4 |
| Urea | 5.0 ± 0.7 |
| Creatinine | 77 ± 10 |
| Sodium | 141 ± 1 |
| Potassium | 4.4 ± 0.4 |
| Chloride | 103 ± 2 |
| Calcium | 2.50 ± 0.09 |
| Phosphorus | 1.16 ± 0.20 |
| AST | 21 ± 9 |
| ALT | 24 ± 14 |
| Hemoglobin (g/L) | 151 ± 17 |
| Hematocrit (L/L) | 0.44 ± 0.04 |
| RBC (x $10^9$/L) | 4.88 ± 0.56 |
| MCV | 89.9 ± 3.5 |
| MCH | 31.0 ± 1.3 |
| MCHC | 346 ± 6 |
| RDW | 12.9 ± 0.2 |
| WBC (x $10^9$/L) | 6.0 ± 1.0 |
| Platelets (x $10^9$/L) | 245 ± 50 |
| Neutrophils (x $10^9$/L) | 3.37 ± 0.88 |
| Lymphocytes (x $10^9$/L) | 1.96 ± 0.33 |
| Monocytes (x $10^9$/L) | 0.52 ± 0.13 |
| Eosinophils (x $10^9$/L) | 0.17 ± 0.22 |
| Basophils (x $10^9$/L) | 0.02 ± 0.03 |
| APTT | 29 ± 2 |
| INR | 1.0 ± 0.1 |

Figure 2. Pharmacokinetics of serum tangeretin (means ± SD)

|  | Formula A | Formula B | P value |
|---|---|---|---|
| Initial conc. (µg/L) | 31.4 ± 5.7 | 37.2 ± 25.6 |  |
| $AUC_{0-48h}$ (µg x min/L) | 2509.6 ± 1092.8 | 1085.8 ± 198.8** | 0.0041 |
| $C_{max}$ (µg/L) | 532.3 ± 335.7 | 76.4 ± 49.9*** | <0.0001 |
| $T_{max}$ (h) | 1.3 ± 0.5 | 1.3 ± 0.8 |  |

Values significantly different by ANOVA followed by Tukey's test. * - $p < 0.05$,  - $p < 0.01$, * - $p < 0.001$.

Figure 3. Pharmacokinetics of serum nobiletin (means ± SD)

|  | Formula A | Formula B | P value |
|---|---|---|---|
| Initial conc. (µg/L) | 49.5 ± 10.6 | 63.5 ± 51.6 |  |
| $AUC_{0-48h}$ (µg x min/L) | 4654.4 ± 1929.3 | 1538.0 ± 249.3*** | <0.0001 |
| $C_{max}$ (µg/L) | 1006.4 ± 555.3 | 51.8 ± 18.8*** | <0.0001 |
| $T_{max}$ (h) | 1.4 ± 0.5 | 1.48 ± 0.8 |  |

Values significantly different by ANOVA followed by Tukey's test. *** - $p < 0.001$.

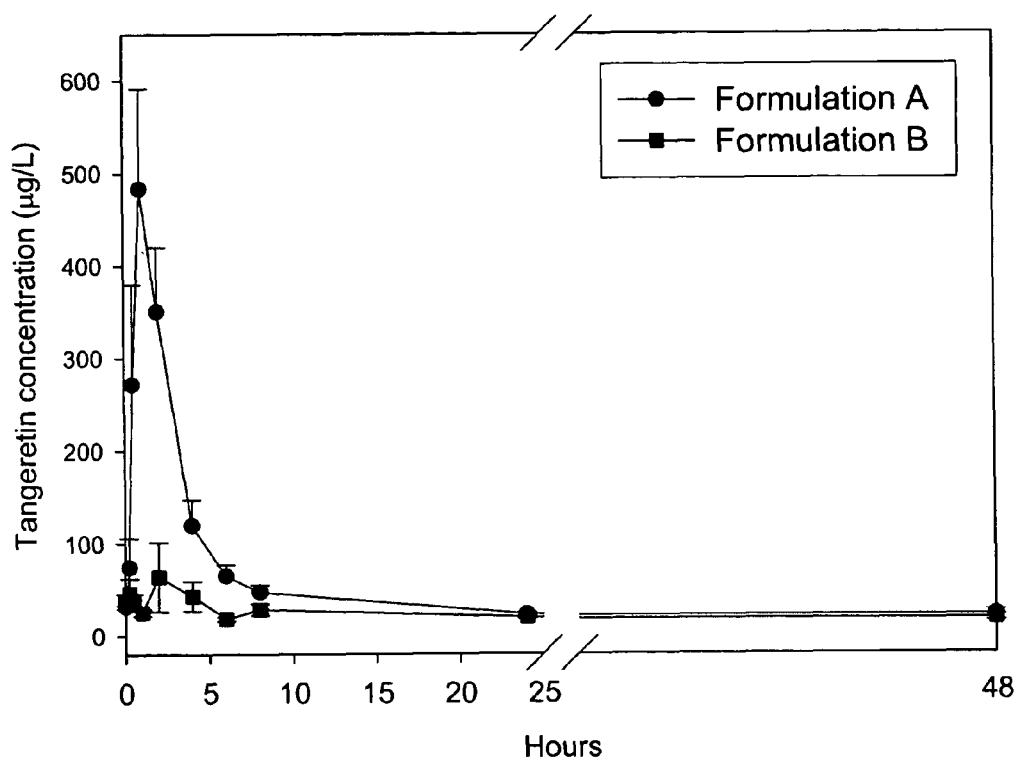
Figure 4. Changes in serum concentrations of tangeretin after a single-dose administration of Sytrinol™ formulations A and B (1053 mg PMFs per each dose). (means ± SEM)

Figure 5 Changes in serum concentrations of nobiletin after a single dose administration of Sytrinol™ formulations A and B (1053 mg PMFs per each dose). (means ± SEM)
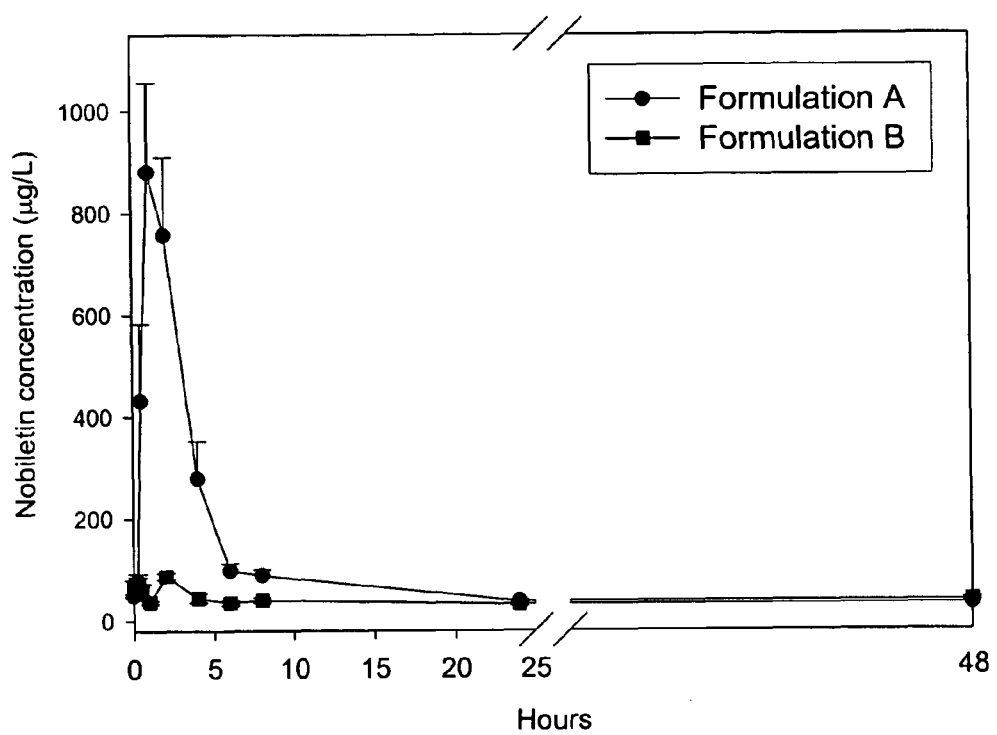

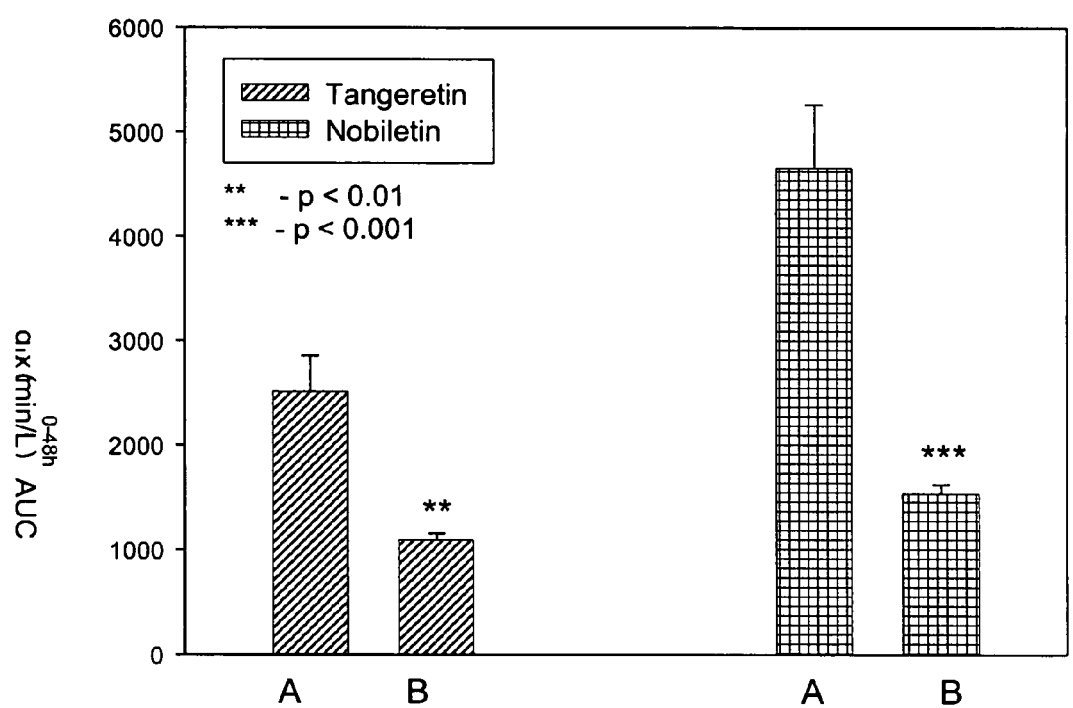
Figure 6. Effects of Sytrinol™ formulations A and B on $AUC_{0-48h}$ of tangeretin and nobiletin (means ± SEM)

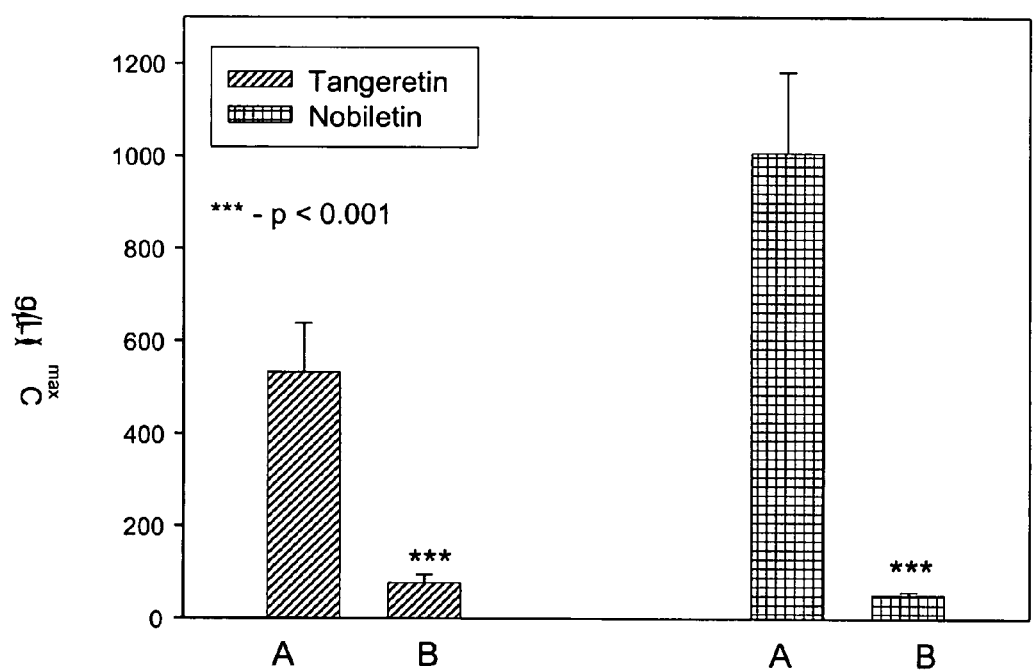
Figure 7. Effects of Sytrinol™ formulations A and B on $C_{max}$ of tangeretin and nobiletin (means ± SEM)

SOFT GEL CAPSULES CONTAINING POLYMETHOXYLATED FLAVONES AND PALM OIL TOCOTRIENOLS

CROSS REFERENCE TO RELATED APPLICATION

This is a Continuation-in-Part Application that claims priority to U.S. Ser. No. 11/145,563, filed on Jun. 3, 2005, entitled "Soft Gel Capsules Containing Polymethoxylated Flavones and Palm Oil Tocotrienols", by Ronald G. Udell, the contents of which are incorporated herein in their entirety.

FIELD OF THE INVENTION

The present invention relates to soft gel formulations that contain efficacious amounts of at least one polymethoxylated flavone and, optionally, at least one palm oil based tocotrienol in an oil carrier or suspending agent. The encapsulated solution of ingredients provides increased bioavailability of the active ingredient in blood plasma relative to administration of the active ingredient(s) in a dry powdered form, such as in a tablet or a two piece hard shell gelatin capsule.

BACKGROUND OF THE INVENTION

Based on data from the Centers for Disease Control and Prevent, approximately 61 million Americans suffer from cardiovascular disease(s). Cardiovascular diseases include a number of disorders, including high blood pressure, coronary heart disease (heart attack, chest pain), stroke, congestive heart failure and defects of the heart and blood vessels.

Coronary artery disease, a form of cardiovascular disease (CVD), is a major cause of death in the United States today. Cerebrovascular disease is believed to be the third. The casual link of both coronary artery and cerebrovascular diseases is related to atherosclerosis. Atherosclerosis is the major cause of the more than one million heart attacks, approximately 400,000 strokes that occur each year and numerous vascular circulation problems. Many patients also suffer from hypertension.

There is a causal relationship between hypercholesterolemia and premature atherosclerosis. Increased levels of plasma cholesterol, primarily low density lipoproteins (LDL) and triglycerides, the greater the risk of subsequent heart attack. Events that appear to lead to atherosclerosis include the formation of lesions (artheromas) in carotid, coronary, and cerebral arteries, and in the aorta. These fatty deposits of cholesterol and cholesteryl ester that are found principally within the smooth muscle cells and macrophages of the intimal layer.

The development of atherosclerosis and cardiovascular disease are modulated by, and/or associated with, LDL oxidation, cyclo-oxygenase (COX) activity, lipoxygenase (LOX) activity, nitric oxide (NO) production, and nitric oxide synthase (NOS) activity. LDL oxidation is involved in the initiation of lesions (atheromas) which occur when macrophages take up oxidatively modified LDL and transform into so-called "foam cells". The enzymes COX and LOX are involved in the arachidonic acid pathway which leads to the production of prostaglandins and thromboxane A2. Thromboxane A2 is known to cause vasoconstriction and platelet aggregation, and thus enhances the progression of atherosclerosis. Nitric oxide is known to inhibit platelet aggregation, monocyte adhesion/chemotaxis and proliferation of vascular smooth muscle, all of which are considered to be responsible for progression of atherosclerosis.

The lipids in blood plasma that are of major clinical importance are cholesterol and triglycerides. Cholesterol is always present as an ingredient in atherosclerotic plaque, along with fatty acid esters of cholesterol, phosphatids, neutral fats and dihydrocholesterol. Cholesterol is not miscible with water. To transport cholesterol in the blood, it is combined or repackaged with a protein. The combination of cholesterol and protein is called a lipoprotein. Very low-density lipoproteins (VLDL or pre-beta-lipoproteins), carry endogenously-synthesized triglycerides, which are removed by muscle, heart, adipose tissue, and other sites. Major remnants of VLDL metabolism are low-density lipoproteins (LDL or beta-lipoproteins). LDLs are catabolized by a mechanism involving receptors in cell membranes, but the major organ binding sites besides the liver are not well defined. It is the LDLs which contain the greatest percentage of cholesterol. These particles, when in excess in the blood, are deposited in the tissues and form a major part of the build-up in the arterial wall to form atherosclerotic plaque which narrows the channels of the coronary arteries which furnish the major blood supply to the heart muscle. High density lipoproteins (HDL or alpha-lipoproteins) contain phospholipids and cholesterol complexed with apolipoproteins, the bulk of which differ from those found in VLDLs and LDLs. It is the HDLs which contain the greatest amount of protein and the smallest amount of cholesterol and are believed to take cholesterol away from cells and transport it back to the liver for processing or removal.

Consequently, elevated blood cholesterol is a major risk factor for coronary heart disease, and many studies have shown that the risk of CHD events can be reduced by lipid-lowering therapy. Prior to the introduction of "statins" lipid-lowering methods were limited essentially to a low saturated fat and cholesterol diet, bile acid sequestrants (cholestyramine and colestipol), nicotinic acid (niacin), fibrates and probucol.

"Statins" are a class of drugs that lowers the level of cholesterol in the blood by reducing the production of cholesterol by the liver. Statins block the enzyme in the liver that is responsible for making cholesterol. This enzyme is called hydroxy-methylglutaryl-coenzyme A reductase (HMG-CoA reductase for short). Therefore, statins are referred to as HMG-CoA reductase inhibitors.

There are currently five statin drugs on the market in the United States and include Lovastatin (Mevacor), Simvastatin (Zocor), Pravastatin (Pravachol), Fluvastatin (Lescol) and Atorvastatin (Lipitor). These drugs lower cholesterol by slowing down the production of cholesterol and by increasing the liver's ability to remove the LDL-cholesterol already in the blood.

Since statins have been introduced into the marketplace, certain side effects have been noted. The most common side effects include nausea, diarrhea, constipation and muscle aches. However, a more serious side effect includes a decrease in the body's supply of coenzyme Q10 (CoQ10), which is an essential nutrient for heart strength and function. Additionally, elevated liver enzymes have been noted in some individuals due to the statin.

Another serious side effect due to administration of statins is known as "Statin myopathy". Statins can cause muscle pain and tenderness referred to as statin myopathy. In severe cases, muscle cells can break down (rhabdomyolysis) and release a protein called myoglobin into the bloodstream. Myoglobin can impair kidney function and lead to kidney failure. Certain drugs when taken with statins can increase the risk of rhabdomyolysis. These drugs include gemfibrozil, erythromycin (Erythrocin), antifungal medications, nefazodone (Serzone), cyclosporine and niacin.

Tangentially, insulin resistance syndrome commonly precedes type 2 diabetes and both disorders are associated with increased risk of heart disease. Insulin resistance is generally defined as an impaired ability of insulin to stimulate glucose uptake and lipolysis and to modulate liver and muscle lipid metabolism. In animals and humans, insulin resistance syndrome leads to hyperinsulinemia and to various defects in lipid metabolism such as enhanced secretion of atherogenic, triacylglycerol-rich very low-density lipoproteins (VLDL), increased liberation of nonesterified fatty acids (NEFA) from adipose tissue and increased accumulation of triacylglycerols in the liver. Other metabolic defects associated with insulin resistance include impairment of endothelium-dependent vasodilation. This last abnormality is largely a consequence of reduced bioavailability of nitric oxide, an important biological mediator involved in protection against atherosclerosis.

As a consequence of the general populations' problems with cardiovascular disease, atherosclerosis, insulin resistance, hyperinsulinemia and/or hypercholesterolemia, there is a need in the art for compositions address one or more of these conditions. Additionally, there is a need for a composition that can help to reduce cholesterol and/or triglycerides from blood plasma without one or more of the disadvantages noted with current drug therapies.

BRIEF SUMMARY OF THE INVENTION

The present invention pertains to the surprising discovery that administration of citrus flavonoids, called polymethoxylated flavones (PMFs), and in particular in combination with a palm oil tocotrienol, in the form of a soft gelatin capsule, provides increased beneficial levels of a PMF in blood plasma, relative to control dosages that are provided in dry powdered forms, i.e., tablets or two piece hard gelatin shell capsules with dried, powdered ingredients.

Unexpectedly, the formulation of a PMF or a PMF with the tocotrienol in combination with an oil carrier provided greater bioavailability of the PMF(s) in blood plasma, when measured by standard analytical techniques. The soft gel formulation provides a PMF(s) or PMF(s)/tocotrienol(s) fluid suspension, or more particularly, a solubilized liquid within the soft gelatin capsule. Not to be limited by theory, the dissolution of the active ingredient(s) (at least one PMF or at least one PMF and at least one tocotrienol) is believed to provide for increased solubility and/or compatibility with the blood plasma that is not achieved by dry powdered formulations.

Not to be limited by theory, it is believed that polymethoxylated flavone(s) block the HMG-CoA reductase enzyme and tocotrienol(s) inhibit production of a cholesterol precursor. Additionally, one or more of the PMFs decrease apoprotein B, a structural protein needed in the synthesis of LDL cholesterol. Moreover, tangeretin and nobiletin decrease diacylglycerol acetyl transferase, a liver enzyme required for endogenous synthesis of triglycerides, hence tangeretin and nobiletin lower the production of triglycerides.

In one aspect, the present invention pertains to soft gelatin capsules that include at least one polymethoxylated flavone, a monomethoxylated flavone and/or a polyhydroxy flavone and an oil based carrier or suspending agent.

In one embodiment, the polymethoxylated flavone (PMF) can be tangeretin. In another embodiment the polymethoxylated flavone can be nobiletin. In another embodiment the polymethoxylated flavone can be both tangeretin and nobiletin and/or additional polymethoxylated, mono-methoxylated flavones and/or hydroxylated flavones. Typically polymethoxylated flavones are citrus flavonoids.

In another embodiment the PMF can be one or more of limocitrin, limocitrin derivatives, quercetin and quercetin derivatives, including but not limited to limocitrin-3,7,4'-trimethylether (5-hydroxy-3,7,8,3',4'-pentamethoxyflavone); limocitrin-3,5,7,4'-tetramethylether (3,5,7,8,3',4'-hexamethoxyflavone); limocitrin-3,5,7,4'-tetraethylether (8,3'-dimethoxy-3,5,7,4'-hexamethoxyflavone); limocitrin-3,7,4'-trimethylether-5-acetate; quercetin tetramethylether (5-hydroxy-3,7,3',4'-tetramethoxyflavone); quercetin-3,5-dimethylether-7,3',4'-tribenzyl ether; quercetin pentamethyl ether (3,5,7,3',4'-pentamethoxyflavone); quercetin-5,7,3',4'-tetramethylether-3-acetate; and quercetin-5,7,3',4'-tetramethylether (3-hydroxy-5,7,3',4'-tetramethoxyflavone); and the naturally occurring polymethoxyflavones: 3,5,6,7,8,3',4'-heptan-ethoxyflavone; 5-desmethylnobiletin (5-hydroxy-6, 7,8,3',4'-pentamethoxyflavone); tetra-O-methylisoscutellarein (5,7,8,4'-tetramethoxyflavone); 5-desmethylsinensetin (5-hydroxy-6,7,3',4'-tetramethoxyflavone); and sinensetin (5,6,7,3',4'-pentamethoxyflavone).

The soft gel capsule can further include a tocotrienol. Typically the tocotrienol is a mixture and often includes at least 3 different tocotrienols known as alpha-tocotrienol, gamma-tocotrienol and delta-tocotrienol. These tocotrienols can be derived from palm oil and are generally known as palm oil tocotrienols.

In one aspect, the soft gel capsule includes at least one PMF and at least one tocotrienol, and in particular the tocotrienols derived from palm oil.

In another aspect, the at least one PMF or at least one PMF and at least one tocotrienol is dissolved in olive oil as the carrier. In one particular aspect, a combination of at least two PMFs and a tocotrienol mixture derived from palm oil are dissolved in olive oil or rice bran oil as suitable carriers.

The various soft gel formulations of the invention can contain, in addition to the PMF(s), optionally the tocotrienol(s) and oil carrier or suspending agent, various additives such as riboflavin, a monoterpene, such as D-limonene, water, titanium dioxide and or chlorophylline.

The present invention further pertains to methods to treat or prevent various afflictions with the soft gel capsule compositions of the invention. Such afflictions include, for example, cardiovascular disease, atherosclerosis and/or hypercholesterolemia.

The present invention also pertains to packaged soft gelatin nutraceutical compositions of the invention used to treat or prevent cardiovascular disease, atherosclerosis and/or hypercholesterolemia.

Typically, the soft gelatin capsule includes at least about 25 mg to about 250 mg total weight of one or more PMF(s) and, optionally, one or more tocotrienol(s) (referred to as active ingredient(s)).

The number of dosages taken per day by the individual in need thereof controls the amount of active ingredient(s) administered. For example, a soft gelatin capsule that contains about 150 mg of active ingredient(s), can be taken once a day to reduce or maintain acceptable levels of lipoproteins and/or triglyercides in blood plasma. Alternatively, two, three or more soft gelatin capsules that contain about 50 mg of active ingredient(s), can be taken during a 24 hour period to treat an individual that has elevated lipoprotein levels/triglyceride levels or wishes to maintain already acceptable levels of these components of the blood.

Advantageously, the active ingredient(s) contained within soft gelatin compositions of the invention can be taken prophylactically prior to the onset of increased levels of lipoproteins and/or triglycerides in an individual's blood plasma.

In another aspect, the present invention provides compositions and methods for the reduction, prevention, and/or treatment of cardiovascular diseases and disorders wherein an effective amount of a soft gelatin composition having at least one solubilized limocitrin and/or quercetin derivative and carrier oil or suspending agent encapsulated within the soft gelatin capsule is administered to reduce, prevent or treat a mammal at high risk for or suffering from a cardiovascular disease.

In yet another aspect, the present invention provides compositions and methods for the reduction, prevention, and/or treatment of cardiovascular diseases or disorders wherein an effective amount of a soft gelatin composition having at least one solubilized flavonoid and carrier oil or suspending agent encapsulated within the soft gelatin capsule is administered to reduce, prevent or treat a mammal at high risk for or suffering from a cardiovascular disease.

In still yet another aspect, the present invention provides compositions and methods for the reduction, prevention, and/or treatment of cardiovascular diseases or disorders wherein an effective amount of a soft gelatin composition having at least one solubilized limocitrin, quercetin derivative, tocotrienol, and/or mixtures thereof and carrier oil or suspending agent encapsulated within the soft gelatin capsule is administered to reduce, prevent or treat a mammal at high risk for or suffering from a cardiovascular disease.

In yet still another aspect, the present invention provides compositions and methods for the reduction, prevention, and/or treatment of cardiovascular diseases or disorders wherein an effective amount of a soft gelatin composition having solubilized at least one limocitrin derivative, quercetin derivative, naturally occurring polymethoxyflavone, tocotrienol, and/or mixtures thereof and carrier oil or suspending agent encapsulated within the soft gelatin capsule, is administered to a mammal to lower serum cholesterol, apo-B, and/or LDL cholesterol.

In another aspect, the present invention provides compositions and methods for the reduction, prevention, and/or treatment of cardiovascular diseases or disorders wherein an effective amount of a soft gelatin composition having at least one solubilized limocitrin derivative, quercetin derivative, naturally occurring polymethoxyaflavone, tocotrienol, and/or mixtures thereof, in combination with a cholesterol-lowering drug and carrier oil or suspending agent encapsulated within the soft gelatin capsule, is administered to a mammal to lower serum cholesterol, apo-B, and/or LDL cholesterol In still yet another aspect, the present invention provides compositions and methods for the reduction, prevention, and/or treatment of cardiovascular diseases or disorders wherein an effective amount of a soft gelatin composition includes at least one solubilized limocitrin derivative, quercetin derivative, naturally occurring polymethoxyaflavone, tocotrienol, and/or mixtures thereof, in combination with a pharmaceutical drug including anti-platelets agents, beta-adrenergic blocking agents, nitrates or calcium channel blockers and carrier oil or suspending agent encapsulated within the soft gelatin capsule.

In still yet another aspect, the present invention provides, compositions and methods for treating hyperlipidemia wherein an effective amount of a soft gelatin composition includes at least one or more solubilized polymethoxyflavone(s) described herein, and optionally a tocotrienol, and carrier oil or suspending agent encapsulated within the soft gelatin capsule, to control hyperlipidemia.

In still yet another aspect, the present invention provides, compositions and methods for treating hypolipidemia wherein an effective amount of a soft gelatin composition includes at least one or more solubilized polymethoxyflavone(s) described herein, and optionally a tocotrienol, and carrier oil or suspending agent encapsulated within the soft gelatin capsule, to control hypolipidemia.

In still yet another aspect, the present invention provides, compositions and methods for treating insulin resistance wherein an effective amount of a soft gelatin composition includes at least one or more solubilized polymethoxyflavone(s) described herein, and optionally a tocotrienol, and carrier oil or suspending agent encapsulated within the soft gelatin capsule, to control insulin resistance.

In yet other aspects, the present invention provides compositions and methods as described above that further include a phytosterol, coenzyme Q-10 and/or EPA or DHA or esters of EPA or DHA.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

BRIEF DESCRIPTION OF THE FIGURES

FIG. 1 depicts baseline characteristics of subjects in Sytrinol™ pharmacokinetics study (mean±SD);

FIG. 2 provides pharmacokinetics of serum tangeretin (means±SD);

FIG. 3 provides pharmacokinetics of serum nobiletin (means±SD);

FIG. 4 shows changes in serum concentrations of tangeretin after a single-dose administration of Sytrinol™ formulations A and B (1053 mg PMFs per each dose);

FIG. 5 shows changes in serum concentrations of nobiletin after a single dose administration of Sytrinol™ formulations A and B (1053 mg PMFs per each dose);

FIG. 6 demonstrates effects of Sytrinol™ formulations A and B on $AUC_{0-48h}$ of tangeretin and nobiletin; and FIG. 7 shows the effects of Sytrinol™ formulations A and B on $C_{max}$ of tangeretin and nobiletin.

DETAILED DESCRIPTION

The present invention pertains to the surprising discovery that soft gelatin formulations that contain at least one polymethoxylated flavone (PMF) (an active ingredient) and, optionally, at least one tocotrienol (a second active ingredient) that is/are dissolved in an oil carrier or suspending agent, provide increased bioavailability of the active ingredient(s) in an individual's blood. In comparison, an individual that is administered a hard two piece gelatin caplet or tablet that contains identical amounts of active ingredient(s) in dry powdered form, has less bioavailable active ingredient(s) in that individual's blood when compared to dosing with the soft gelatin equivalent.

The term "polymethoxylated flavones" is recognized in the art and is intended to include those compounds that are citrus flavonoids that are methoxylated. Flavonoids are polyphenolic compounds having a basic 15-carbon skeleton consisting of two benzene rings joined by a linear three carbon chain, and can be represented as C6-C3-C6. Flavonoids from citrus fruits have a benzo-gamma-pyrone derivative at the C3 position that belong to two classes named flavanones and flavones. The most prevalent flavanones are hesperetin from oranges and naringenin from grapefruit. Two polymethoxylated flavones (PMFs) are tangeretin and nobiletin, found in tangerines sweet orange peel (*Citrus sinesis*) and bitter orange peel (*Citrus aurantium*).

As stated above, flavonoids are polyphenolic compounds that occur ubiquitously in plant foods especially in orange, grapefruit and tangerine. Therefore, "polymethoxylated" refers to the methylated phenolic sites about the parent molecule. Suitable examples of polymethoxylated flavones that are citrus flavonoids include tangeretin and nobiletin having structural formulae:

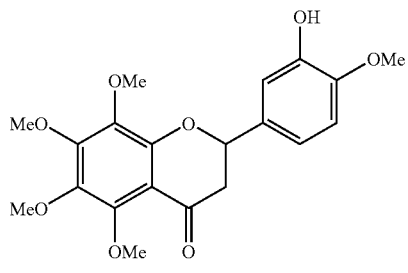

Tangeretin

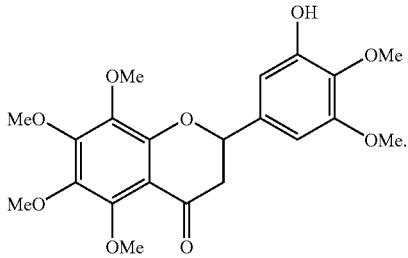

Nobiletin

Naturally occurring polymethoxyflavones also include compounds that such as limocitrin and quercetin and derivatives that can be chemically synthesized. These include, for example:
limocitrin-3,7,4'-trimethylether (5-hydroxy-3,7,8,3',4'-pentamethoxyflavone)
limocitrin-3,5,7,4'-tetramethylether(3,5,7,8,3'4'-hexamethoxyflavone)
limocitrin-3,5,7,4'-tetraethylether(8,3'-dimethoxy-3,5,7,4'-tetraethoxylfavone)
limocitrin 3,7,4'-trimethylether-5-acetate
quercetin tetramethylether (5-hydroxy-3,7,3',4'-tetramethoxyflavone)
quercetin 3,5-dimethylether-7,3'4'-tribenzyl ether
quercetin pentamethylether (3,5,7,3',4'-pentamethoxyflavone)
quercetin-5,7,3',4'-tetramethylether-3-acetate
quercetin-5,7,3',4'-tetramethylether (3-hydroxy-5,7,3',4'-tetramethoxyflavone)
3,5,6,7,8,3',4'-heptamethoxyflavone
5-desmethylnobiletin (5-hydroxy-6,7,8,3',4'-pentamethoxyflavone)
tetra-O-methylisoscutellarein (5,7,8,4'-tetramethoxyflavone)
5-desmethylsinensetin (5-hydroxy-6,7,3',4'-tetramethoxyflavone) and
sinensetin (5,6,7,3',4'-pentamethoxyflavone).

Suitable examples of mono methoxylated or hydroxylated flavonoids, useful for preparing soft gel capsules and to treat the conditions noted herein, include hesperetin and naringenin, respectively having structural formulae:

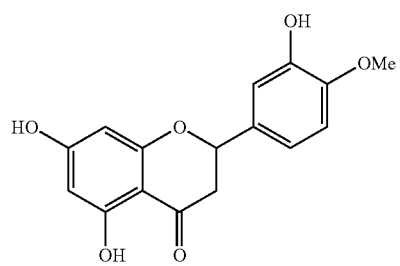

Hesperetin

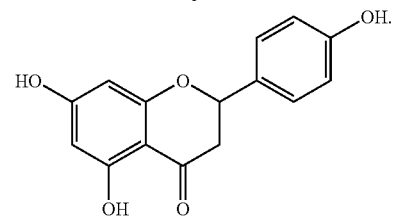

Naringenin

The term "tocotrienols" is recognized in the art and are known to be present in palm oil and are a form of vitamin E having an unsaturated side chain. They include, but are not limited to alpha-tocotrienol, gamma-tocotrienol or delta-tocotrienol as illustrated by the following formulae:

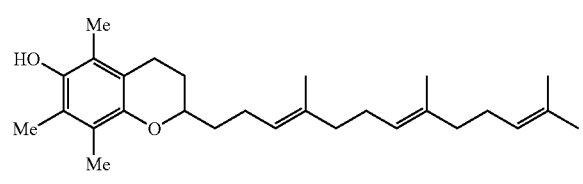

alpha-tocotrienol

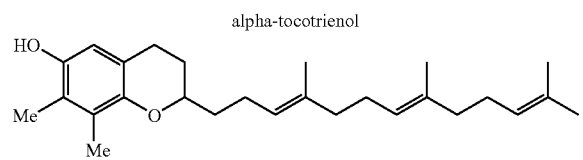

gamma-tocotrienol

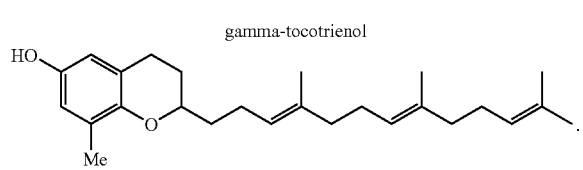

delta-tocotrienol

A suitable proprietary commercially available mixture of PMF's and tocotrienols is Sytrinol™, available from KGK Synergize, 255 Queens Avenue, London, Ontario, Canada. The teachings of U.S. Pat. Nos. 6,251,400, 6,239,114 and US Publication Nos. 2004/0214882, published Oct. 28, 2004 and 2004/0152641, published Aug. 5, 2004 are incorporated herein in the entirety.

In one embodiment, a solubilized mixture of Sytrinol™, extra virgin olive oil, yellow bees wax and, optionally, D-Limonene are encapsulated within a soft gelatin capsule. Not to be limited by theory, it is believed that the dissolution of the PMF's and tocotrienols within the carrier system (olive oil and/or D-Limonene) within the soft gelatin capsule facilitates the active ingredients to become more bioavailable when administered to an individual, when compared to ingestion of dry powdered Sytrinol™ in a traditional tablet, caplet or hard shelled gelatin caplet.

Formulation of the active ingredients can be accomplished by many methods known in the art. For example, the active ingredient(s) can be formulated in a suspension, an emulsion, or a solution within a soft gelatin capsule that encapsulates the liquid. Often the formulation will include an acceptable carrier, such as an oil, or other suspending agent.

Suitable carriers include but are not limited to, for example, fatty acids, esters and salts thereof, that can be derived from any source, including, without limitation, natural or synthetic oils, fats, waxes or combinations thereof. Moreover, the fatty acids can be derived, without limitation, from non-hydrogenated oils, partially hydrogenated oils, fully hydrogenated oils or combinations thereof. Non-limiting exemplary sources of fatty acids (their esters and salts) include seed oil, fish or marine oil, canola oil, vegetable oil, safflower oil, sunflower oil, nasturtium seed oil, mustard seed oil, olive oil, sesame oil, soybean oil, corn oil, peanut oil, cottonseed oil, rice bran oil, babassu nut oil, palm oil, low erucic rapeseed oil, palm kernel oil, lupin oil, coconut oil, flaxseed oil, evening primrose oil, jojoba, tallow, beef tallow, butter, chicken fat, lard, dairy butterfat, shea butter or combinations thereof.

Suitable amounts of Sytrinol™ used in the compositions of the invention range from about 25 milligrams to about 400 milligrams, and in particular from about 50 milligrams to about 300 milligrams, and more particularly from about 100 to about 200 milligrams on a weight basis.

Specific non-limiting exemplary fish or marine oil sources include shellfish oil, tuna oil, mackerel oil, salmon oil, menhaden, anchovy, herring, trout, sardines or combinations thereof. In particular, the source of the fatty acids is fish or marine oil (DHA or EPA), soybean oil or flaxseed oil. The DHA or EPA can be in the form of an ester, such as a methyl ester. Alternatively or in combination with one of the above identified carriers, beeswax can be used as a suitable carrier, as well as suspending agents such as silica (silicon dioxide).

In embodiments where DHA or EPA or mixtures thereof (as an acid, an ester or mixtures thereof) are included in a formulation of the invention, between about 10 milligrams and about 200 milligrams of EPA is included in a composition of the invention, in particular, between about 25 milligrams and about 150 milligrams, and more particularly between about 50 milligrams and about 100 milligrams on a weight basis.

Suitable ranges for DHA are from about 5 milligrams about 200 milligrams, in particular between about 15 milligrams and about 150 milligrams, and more particularly between about 25 milligrams and about 100 milligrams on a weight basis.

Suitable ranges for Marine Lipid Oil are from about 100 milligrams and about 1000 milligrams, in particular from about 150 milligrams to about 750 milligrams, and more particularly from about 250 milligrams to about 500 milligrams on a weight basis.

The formulations of the invention can further include one or more phytosterols. Phytosterols are known as plant sterols and occur naturally as a class of compounds found in the cells and membranes of plants. These plant lipid-like compounds are present in grains, fruits and vegetables. There are approximately 250 different phytosterols and related compounds in plant and marine materials with the most common being beta-sitosterol, stigmasterol, and campesterol. Phytosterols help to block the absorption of cholesterol and reduce blood cholesterol levels.

Phytosterols have a molecular structure similar to dietary and endogenously secreted cholesterol. The most abundant phytosterols (sitosterol, campesterol, and stigmasterol) differ from cholesterol by the nature of the side chain or the presence of an extra double bond within the cyclic carbocycle. A suitable commercial source of phytosterols is from SourceOne, Chicago Ill. (SterolSource™, Phytosterols, 95% containing greater than 40% greater than 20% and greater than 17% by weight of beta-sitosterol, campesterol and stigmasterol, respectively).

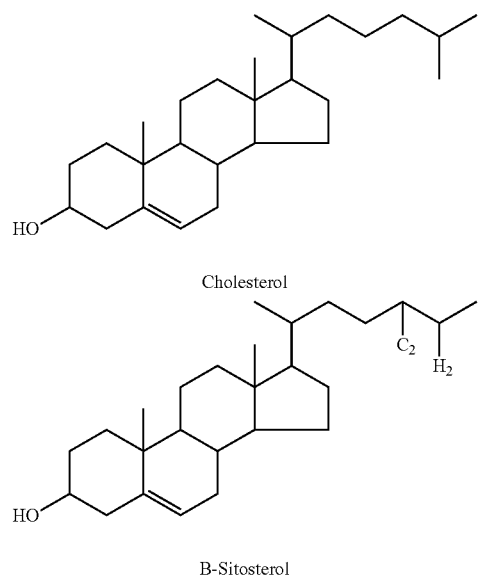

Cholesterol

B-Sitosterol

Generally, between about 10 milligrams and about 400 milligrams of a phytosterol is included in a composition of the invention, in particular, between about 25 milligrams and about 300 milligrams, and more particularly between about 50 milligrams and about 200 milligrams on a weight basis.

Because cholesterol and phytosterol molecules are similar, the human body does not differentiate between the two molecules. Therefore, phytosterols compete with cholesterol for absorption in the small intestine but the phytosterols are not absorbed by the body.

Cholesterol is absorbed in the upper third of the intestine. Phytosterols block the absorption of dietary cholesterol into the bloodstream and inhibit the re-absorption of cholesterol from bile acids in the digestive process, thus reducing the amount of cholesterol entering the bloodstream. The absorption rate of phytosterols is approximately 1/10th that of cholesterol, meaning that the pathways in the intestine are occupied by phytosterols for an extended period of time, which makes the blocking process even more effective.

The combination of phytosterols with a flavone and/or a tocotrienol is an effective way to reduce cholesterol.

The formulations of the invention are considered dietary supplements useful to increase the amounts of levels of PMF's and/or tocotrienols, in individuals in need thereof.

Another important additive is coenzyme Q-10 (CoQ-10) and/or analogs thereof. CoQ-10 (coenzyme Q10) is a fat-soluble quinone that is structurally similar to vitamin K and commonly known as ubiquinone. CoQ-10 is found in most living organisms, and is essential for the production of cellular energy. CoQ-10 (2,3 dimethyl-5 methyl-6-decaprenyl benzoquinone) is an endogenous antioxidant found in small amounts in meats and seafood. Although CoQ-10 is found in all human cells, the highest concentrations of CoQ-10 occur in the heart, liver, kidneys, and pancreas. It is found naturally in the organs of many mammalian species.

CoQ-10 is an important nutrient because it lies within the membrane of a cell organelle called the mitochondria. Mitochondria are known as the "power house" of the cell because of their ability to produce cellular energy, or ATP, by shuttling protons derived from nutrient breakdown through the process of aerobic (oxygen) metabolism. CoQ-10 also has a secondary role as an antioxidant. CoQ-10, due to the involvement in ATP synthesis, affects the function of almost all cells in the body, making it essential for the health of all human tissues and organs. CoQ-10 particularly effects the cells that are the most metabolically active: heart, immune system, gingiva, and gastric mucosa CoQ-10 analogs include reduced and semi-reduced CoQ-10 and ubiquinone derivatives described, for example, in WO 8803015, the teachings of which are incorporated herein by reference.

Generally, between about 10 milligrams and about 300 milligrams of CoQ-10 or an analog is included in a composition of the invention, in particular, between about 15 milligrams and about 200 milligrams, and more particularly between about 20 milligrams and about 100 milligrams on a weight basis.

Alternatively, the formulations of the invention are also considered to be nutraceuticals. The term "nutraceutical" is recognized in the art and is intended to describe specific chemical compounds found in foods that may prevent or treat disease. PMF and/or tocotrienol extracts are considered to be such compounds.

Polycosinol, red yeast rice, gugulipid, pantethine, garlic, chromium, carnitine, artichoke leaf, green tea, *Gymnema sylvestre*, grape seed extract, pine bark extract, ginseng and silymarin are additional active ingredients that can be used in the present formulations to treat one or more of the ailments, including lowering cholesterol, indicated within the present specification.

Policosanol (polycosanol) consists of a mixture of fatty alcohols derived from waxes of sugar cane (the main source of policosanol,) yams, and beeswax. The main ingredient of policosanol is octanosol. These active substances act to lower cholesterol levels by several mechanisms which include blocking the formation of cholesterol in the liver.

Not to be limited by theory, it is believed that the alcohols in policosanol act on cholesterol metabolism in the liver, but at a different part of the metabolic pathway than statins. Many animal studies with policosanol demonstrate a cholesterol lowering effect, and more recently human studies have suggested that LDL cholesterol can be reduced to a degree similar to that achieved with statins, and that HDL cholesterol can be increased by as much as 10-25% (an effect difficult to achieve with statins). Policosanol also reduces the platelet aggregation (i.e., the "stickiness" of platelets, the blood elements that promote blood clotting).

Generally, between about 5 milligrams and about 50 milligrams of policosanol is included in a composition of the invention, in particular, between about 10 milligrams and about 30 milligrams, and more particularly between about 10 milligrams and about 20 milligrams on a weight basis.

Typically a composition is provided that includes about 10 milligrams of policosanol. Generally, two, three, four or more dosages of the composition are taken over the course of a day to provide between about 10 and 20 milligrams of policosanol.

Red yeast rice (extract) is an Asian dietary staple made by fermenting red yeast (*Monascus purpureus*) on rice and is recognized as a cholesterol-lowering agent. This is due in part to a careful fermentation process that yields statins, compounds known to reduce cholesterol levels.

As a substance, red yeast rice extract has a number of heart-healthy benefits. It helps reduce total cholesterol levels, lower levels of LDL cholesterol, increase levels of HDL cholesterol, and lower levels of triglycerides. Not to be limited by theory, it appears that red yeast rice (and its extracts) accomplish this by restricting the liver's production of cholesterol. The compound responsible for this effect, mevinolin, is chemically identical to the cholesterol lowering compound known as lovastatin, which is sold as the prescription drug Mevacor. Additionally, unsaturated fatty acids in red yeast rice extract are also believed to be beneficial, possibly by lowering triglycerides.

Generally, between about 300 milligrams and about 1200 milligrams of red yeast rice extract is included in a composition of the invention, in particular, between about 400 milligrams and about 1000 milligrams, and more particularly between about 500 milligrams and about 800 milligrams on a weight basis.

Typically a composition is provided that includes about 300 milligrams of red yeast rice extract. Generally, two, three, four or more dosages of the composition are taken over the course of a day to provide between about 600 and 1200 milligrams of read yeast rice extract.

Gugulipid is an extract from the mukul myrrh tree (*Commiphora mukul*) that is native to India. It is a purified extract standardized for compounds known as guggulsterones. The active compounds in gugulipid believed to be responsible for the cholesterol-lowering properties are two steroids: E- and Z-guggulsterone. Several clinical studies have shown gugulipid has an ability to lower both cholesterol and triglyceride levels.

The mechanism of action for gugulipid's cholesterol lowering action is its ability to increase the liver's ability to breakdown cholesterol. The dosage of gugulipid is based on its guggulsterone content.

Related benefits are its ability to prevent plaque from forming in arterial walls, which can lead to heart attacks if unchecked. Moreover, it acts as an anti-coagulant by inhibiting blood platelets from clumping together, and, therefore, affords protection against blood clots.

Gugulipid also harbors antioxidant properties; antioxidants scavenge free radicals, which are highly reactive substances that damage cells, leading to premature disease and aging.

Generally, between about 100 milligrams and about 700 milligrams of gugulipid is included in a composition of the invention, in particular, between about 200 milligrams and about 600 milligrams, and more particularly between about 250 milligrams and about 500 milligrams on a weight basis.

Typically a composition is provided that includes about 250 milligrams of gugulipid. Generally, two, three, four or more dosages of the composition are taken over the course of a day to provide between about 500 and 1000 milligrams of gugulipid.

Garlic can help reduce cholesterol. Garlic is a proven antioxidant and this property helps to prevent LDLs from being oxidized. In this way the cholesterol build up is believed to be reduced by garlic.

Generally, between about 200 milligrams and about 500 milligrams of garlic is included in a composition of the invention, in particular, between about 250 milligrams and about 400 milligrams, and more particularly between about 300 milligrams and about 350 milligrams on a weight basis.

Typically a composition is provided that includes about 250 milligrams of garlic. Generally, two, three, four or more dosages of the composition are taken over the course of a day to provide between about 500 and 4000 milligrams of garlic.

Pantethine is a combination of pantothenic acid (vitamin B-5) and beta mercaptoethylamine. Panteteine is the precursor to coenzyme A, the critical starting point in the Krebs energy production cycle.

Pantethine is the disulfide dimer of pantetheine, the 4'-phosphate derivative of which is an intermediate in the conversion of the B vitamin pantothenic acid to coenzyme A. Pantethine is found naturally in small quantities in most forms of life, and therefore, in food sources. Pantethine has lipid-lowering effects. Pantethine is also known as D-bis(N-pantothenyl-beta-aminoethyl)disulfide and (R)-N,N'-[dithiobis (ethyleneimino-carbonylethylene]bis(2,4-dihydroxy-3,3-dimethylbutyramide). Its molecular formula is $C_{22}H_{42}N_4O_8S_2$ and its molecular weight is 554.73 daltons.

Pantethine has been found to decrease serum levels of total cholesterol, low-density lipoprotein cholesterol (LDL-C), apolipoprotein B and triglycerides. It has also been found to increase high-density lipoprotein cholesterol (HDL-C) and apolipoprotein A1 levels. In isolated hepatocytes, pantethine has been shown to inhibit both cholesterol and fatty acid synthesis. It is believed that pantethine, by acting as a precursor of coenzyme A, may enhance the beta-oxidation of fatty acids.

Generally, between about 200 milligrams and about 500 milligrams of pantethine is included in a composition of the invention, in particular, between about 200 milligrams and about 400 milligrams, and more particularly between about 250 milligrams and about 300 milligrams on a weight basis.

Typically a composition is provided that includes about 500 milligrams of pantethine. Generally, two, three, four or more dosages of the composition are taken over the course of a day to provide between about 500 and 1000 milligrams of pantethine.

Chromium lowers total and LDL cholesterol levels and raises HDL cholesterol levels in the blood, particularly in people with high cholesterol.

Chromium is generally utilized as a complex. There are various chromium complexes available that can be included in the compositions of the invention. These include, but are not limited to, chromium chloride, chromium picolinate, chromium chloride, chromium nicotinate, and high-chromium yeast.

For example, chromium polynicotinate, in particular, is a trace mineral that helps regulate carbohydrate metabolism. Since all carbohydrates are reduced in the body into simple glucose, chromium polynicotinate provides the go-between action by "plugging" serum glucose from the bloodstream directly to the muscle cell. Chromium is a necessary component for carbohydrate metabolism, glucose regulation, and energy production.

Chromium polynicotinate is a mineral utilized in the regulation of blood sugar. It is involved in the metabolism of glucose and is a key component for energy. The ability to maintain stable blood sugar levels is often jeopardized by diets that are often high in white flour, refined sugar and junk food. Chromium polynicotinate facilitates and/or stimulates the metabolism of sugar, fat and cholesterol in the body, as well as the function of insulin.

Chromium picolinate can lead to significant improvements in body composition resulting from fat loss, particularly for individuals who may not be as aggressive in making lifestyle changes such as reducing caloric intake or increasing their physical activity. It is believed that chromium picolinate's positive effect on body composition is through its ability to improve insulin utilization, thereby reducing fat deposition and resulting in improving entry of glucose and amino acids into muscle cells.

Generally, between about 200 micrograms and about 600 micrograms of chromium is included in a composition of the invention, in particular, between about 200 micrograms and about 400 micrograms, and more particularly between about 250 micrograms and about 300 micrograms on a weight basis.

Typically a composition is provided that includes about 200 micrograms of chromium. Generally, two, three, four or more dosages of the composition are taken over the course of a day to provide between about 200 and 600 micrograms of chromium.

Carnitine is a water-soluble vitamin like compound that the body utilizes to turn fat into energy. Carnitine works as part of an enzymatic complex formed from carnitine acyltransferase 1, carnitine translocase and carnitine transferase 11.

Carnitine is often used for heart conditions and it may be useful to treat angina or chest pain. Research has also shown that carnitine is also useful in the treatment of congestive heart failure, to reduce cholesterol (LDL), increase high density lipoprotein (HDL), and for intermittent claudication. Although carnitine does not increase blood flow, it is believe that it helps muscles to better function under difficult painful circumstances, such as those associated with claudication.

The actions of carnitine and CoQ-10 are interrelated. In fact, carnitine, through beta-oxidation of fatty acids, is able to restore the energy supplies necessary for cell-life, whereas Coenzyme Q is able to restore the ATP supplies necessary for the energetic metabolic processes of the cell.

L-carnitine is recognized in the art and facilitates transport of materials through the mitochondrial membrane. L-carnitine is an essential fatty acid metabolism cofactor that helps to move fatty acids to the mitochondria from the cytoplasm. This is an important factor as this is where CoQ-10 uptake occurs.

In one aspect of the present invention, L-carnitine is included in soft gel formulations in combination with CoQ-10. Suitable ratios of L-carnitine and CoQ-10 are known in the art and include those described in U.S. Pat. No. 4,599,232, issued to Sigma Tau Industrie Faramaceutiche Riunite S.p.A. on Jul. 8, 1986, the teachings of which are incorporated herein in their entirety. In particular, combinations of limonene, CoQ-10 and L-carnitine in soft gel formulations are of importance.

The term "carnitine" is also known as 3-Carboxy-2-hydroxy-N,N,N-trimethyl-1-propanaminium hydroxide, inner salt; (3-carboxy-2-hydroxypropyl)trimethylammonium hydroxide, inner salt; gamma-amino-beta-hydroxybutyric acid trimethylbetaine; gamma-trimethyl-beta-hydroxybutyrobetaine; 3-hydroxy-4-(trimethyl-ammonio)butanoate. See The Merck Index (1989), p. 281 and references cited therein. Therefore, "carnitine" and "carnitine analogs" includes, but is not limited to racemic or essentially pure L-carnitine (carnitine), or a corresponding alkanoyl-carnitine such as e.g. acetyl-carnitine or propionyl-carnitine, or a suitable salt of such compounds such as e.g. L-carnitine tartrate, L-carnitine fumarate, L-carnitine-magnesium-citrate, acetyl-L-carnitine tartrate, acetyl-L-carnitine-magnesium-citrate, or any mixture of the afore mentioned compounds.

Carnitine and carnitine analogs also include those described in U.S. Pat. Nos. 5,362,753, 4,687,782, 5,030,458, 5,030,657, 4,343,816, 5,560,928, 5,504,072, 5,391,550 and 5,240,961, the teachings of which are incorporated herein by reference in their entirety.

Generally, between about 100 milligrams and about 300 milligrams of carnitine is included in a composition of the invention, in particular, between about 200 milligrams and about 300 milligrams, and more particularly between about 220 milligrams and about 250 milligrams on a weight basis.

Typically a composition is provided that includes about 250 milligrams of carnitine. Generally, two, three, four or more dosages of the composition are taken over the course of a day to provide between about 500 and 2000 milligrams of carnitine.

Artichoke (cynara scolymus) has a number of beneficial effects, and has been used in jaundice and liver insufficiency as well as for cholesterol reduction. It is considered that artichoke inhibits oxidation of low density lipoprotein and reduces cholesterol biosynthesis. Active components of artichoke are cynarine and luteolin.

The leaves of the artichoke contain a high content of pharmacologically active ingredients, including three essential groups consisting of caffeeolyquinic acid (CCS), flavonoids and bitter substances. Within these groups are constituents such as caffeic acid, chlorogenic acid, cynarine (1,5-dicaffeolyquinic acid), luteolin, and the glycosides scolymoside and cynaroside. Among the most important of the CCS are the 1,3-Di-O-CCS, choloregenic acid and the Cynarin.

Generally, between about 100 milligrams and about 300 milligrams of artichoke is included in a composition of the invention, in particular, between about 200 milligrams and about 300 milligrams, and more particularly between about 220 milligrams and about 250 milligrams on a weight basis.

Typically a composition is provided that includes about 300 milligrams of artichoke. Generally, two, three, four or more dosages of the composition are taken over the course of a day to provide between about 500 and 1200 milligrams of artichoke.

Green tea is an herb (*Camellia sinensis*). Green tea originated in China, Japan and other parts of Asia. The leaf of the plant is used in creating the extract which is potent and bioflavonoid-rich. This herb is used primarily for its free-radical scavenging capabilities.

Green tea is prepared by picking, lightly steaming and allowing the leaves to dry. The active constituents in green tea are a family of polyphenols (catechins) and flavonols which possess potent antioxidant activity. Tannins, large polyphenol molecules, form the bulk of the active compounds in green tea, with catechins comprising nearly 90%. Several catechins are present in significant quantities; epicatechin (EC), epigallocatechin (EGC), epicatechin gallate (ECG) and epigallocatechin gallate (EGCG). EGCG makes up about 10-50% of the total catechin content and appears to be the most powerful of the catechins with antioxidant activity about 25-100 times more potent than vitamins C and E.

Generally, between about 100 milligrams and about 300 milligrams of green tea is included in a composition of the invention, in particular, between about 200 milligrams and about 300 milligrams, and more particularly between about 220 milligrams and about 250 milligrams on a weight basis.

Typically a composition is provided that includes about 100 milligrams of green tea. Generally, two, three, four or more dosages of the composition are taken over the course of a day to provide between about 100 and 300 milligrams of green tea.

*Gymnema sylvestre*, also known as Gurmarbooti or Gurmar, is a woody climbing plant that grows in the tropical forests of central and southern India. Cholesterol reducing activity is attributed to members of a family of substances called gymnemic acids.

Gymnemic acids, the active ingredients, are thought to have a gradual blood sugar lowering effect that may result from enhancing the overall function and health of pancreatic insulin releasing cells and reducing insulin resistance. As a liquid, gymnema blocks the absorption of dietary fats into the bloodstream.

Generally, between about 100 milligrams and about 300 milligrams of *Gymnema sylvestre* is included in a composition of the invention, in particular, between about 200 milligrams and about 300 milligrams, and more particularly between about 220 milligrams and about 250 milligrams on a weight basis.

Typically a composition is provided that includes about 300 milligrams of *Gymnema sylvestre*. Generally, two, three, four or more dosages of the composition are taken over the course of a day to provide between about 500 and 1000 milligrams of *Gymnema sylvestre*.

Grape seed extract includes specialized flavonoids called oligomeric proanthocyanidins (OPCs). Studies suggest grape seed helps improve blood circulation, prevent atherosclerosis, lowers blood pressure and decreases low density lipoprotein cholesterol levels and increases high density lipoprotein levels.

The OPCs are chemically known as flavonoids or polyphenols, which can differ substantially based on their polymer arrangement. For example, polyphenols can exist in single (monomers), double (dimers), triple (trimers), quadruple (tetramers) and even longer cyanidin chains (tannins). Any chain length from 2-7 or so is referred to as an oligomer and longer chains are generally referred to as polymers.

Generally, between about 100 milligrams and about 300 milligrams of grape seed extract is included in a composition of the invention, in particular, between about 200 milligrams and about 300 milligrams, and more particularly between about 220 milligrams and about 250 milligrams on a weight basis.

Typically a composition is provided that includes about 100 milligrams of grape seed extract. Generally, two, three, four or more dosages of the composition are taken over the course of a day to provide between about 100 and 300 milligrams of grape seed extract.

Pine bark extract can be included in the compositions of the invention to reduce low density lipoproteins and to help strengthen blood vessel walls. Pine bark extract is also known as French Marine Pine Bark Extract, French Maritime Pine Bark Extract, Leucoanthocyanidins, OPC, Oligomeric Proanthocyanidins, PCO, Pine Bark, *Pinus maritima, Pinus pinaster*, Procyandiol Oligomers, Procyanodolic Oligomers, Pycnogenol, and Pygenol.

Generally, between about 100 milligrams and about 300 milligrams of pine bark extract is included in a composition of the invention, in particular, between about 200 milligrams and about 300 milligrams, and more particularly between about 220 milligrams and about 250 milligrams on a weight basis.

Typically a composition is provided that includes about 100 milligrams of pine bark extract. Generally, two, three, four or more dosages of the composition are taken over the course of a day to provide between about 100 and 300 milligrams of pine bark extract.

*Panax ginseng* is also called ginseng, Korean ginseng, schinsent, or ninjin. Ginseng is an adaptogen that has been used to lower cholesterol, balance the metabolism, increase energy levels, and stimulate the immune system.

Ginseng is characterized by the presence of ginsenoside. Ginsenosides are a class of steroid-like compounds, triterpene saponins, found exclusively in ginseng.

Generally, between about 25 milligrams and about 200 milligrams of ginseng is included in a composition of the invention, in particular, between about 50 milligrams and about 150 milligrams, and more particularly between about 75 milligrams and about 100 milligrams on a weight basis.

Typically a composition is provided that includes about 50 milligrams of ginseng. Generally, two, three, four or more dosages of the composition are taken over the course of a day to provide between about 25 and 200 milligrams of ginseng.

Extracts of Milk Thistle protect against liver toxins through the action of antihepatotoxic (liver protectant) compounds commonly referred to as silymarin. Silymarin has been shown to consist of a large number of flavonolignans, including silybin, isosilybin, dehydrosilybin, silydianin and silychristin. Silymarin, and component silybin, function as antioxidants, protecting cell membranes from free-radical-mediated oxidative damage. Both silymarin and silybin protect red blood cell membranes against lipid peroxidation and hemolysis (breaking down of the red blood cells) caused by certain red blood cell poisons and have also been found to reduce total serum cholesterol.

Generally, between about 25 milligrams and about 200 milligrams of silymarin is included in a composition of the invention, in particular, between about 50 milligrams and about 150 milligrams, and more particularly between about 75 milligrams and about 100 milligrams on a weight basis.

Typically a composition is provided that includes about 100 milligrams of silymarin. Generally, two, three, four or more dosages of the composition are taken over the course of a day to provide between about 240 and 500 milligrams of silymarin.

The term "monoterpene" as used herein, refers to a compound having a 10-carbon skeleton with non-linear branches. A monoterpene refers to a compound with two isoprene units connected in a head-to-end manner. The term "monoterpene" is also intended to include "monoterpenoid", which refers to a monoterpene-like substance and may be used loosely herein to refer collectively to monoterpenoid derivatives as well as monoterpenoid analogs. Monoterpenoids can therefore include monoterpenes, alcohols, ketones, aldehydes, ethers, acids, hydrocarbons without an oxygen functional group, and so forth.

It is common practice to refer to certain phenolic compounds, such as eugenol, thymol and carvacrol, as monoterpenoids because their function is essentially the same as a monoterpenoid. However, these compounds are not technically "monoterpenoids" (or "monoterpenes") because they are not synthesized by the same isoprene biosynthesis pathway, but rather by production of phenols from tyrosine. However, common practice will be followed herein. Suitable examples of monoterpenes include, but are not limited to, limonene, pinene, cintronellol, terpinene, nerol, menthane, carveol, S-linalool, safrol, cinnamic acid, apiol, geraniol, thymol, citral, carvone, camphor, etc. and derivatives thereof. For information about the structure and synthesis of terpenes, including terpenes of the invention, see Kirk-Othmer Encyclopedia of Chemical Technology, Mark, et al., eds., 22:709-762 3d Ed (1983), the teachings of which are incorporated herein in their entirety.

In particular, suitable limonene derivatives include perillyl alcohol, perillic acid, cis-dihydroperillic acid, trans-dihydroperillic acid, methyl esters of perillic acid, methyl esters of dihydroperillic acid, limonene-2-diol, uroterpenol, and combinations thereof.

The soft gel capsule formulations of the invention can further include various ingredients to help stabilize, or help promote the bioavailability of the active ingredient(s), or serve as additional nutrients to an individual's diet. Suitable additives can include vitamins and biologically-acceptable minerals. Non-limiting examples of vitamins include vitamin A, B vitamins, vitamin C, vitamin D, vitamin E, vitamin K and folic acid. Non-limiting examples of minerals include iron, calcium, magnesium, potassium, copper, chromium, zinc, molybdenum, iodine, boron, selenium, manganese, derivatives thereof or combinations thereof. These vitamins and minerals may be from any source or combination of sources, without limitation. Non-limiting exemplary B vitamins include, without limitation, thiamine, niacinamide, pyridoxine, riboflavin, cyanocobalamin, biotin, pantothenic acid or combinations thereof.

Vitamin(s), if present, are present in the composition of the invention in an amount ranging from about 5 mg to about 500 mg. More particularly, the vitamin(s) is present in an amount ranging from about 10 mg to about 400 mg. Even more specifically, the vitamin(s) is present from about 250 mg to about 400 mg. Most specifically, the vitamin(s) is present in an amount ranging from about 10 mg to about 50 mg. For example, B vitamins are in usually incorporated in the range of about 1 milligram to about 10 milligrams, i.e., from about 3 micrograms to about 50 micrograms of B12. Folic acid, for example, is generally incorporated in a range of about 50 to about 400 micrograms, biotin is generally incorporated in a range of about 25 to about 700 micrograms and cyanocobalamin is incorporated in a range of about 3 micrograms to about 50 micrograms.

Mineral(s), if present, are present in the soft gel capsule compositions of the invention in an amount ranging from about 25 mg to about 1000 mg. More particularly, the mineral(s) are present in the composition ranging from about 25 mg to about 500 mg. Even more particularly, the mineral(s) are present in the composition in an amount ranging from about 100 mg to about 600 mg.

Various additives can be incorporated into the present soft gel capsule compositions. Optional additives of the present composition include, without limitation, phospholipids, L-carnitine, starches, sugars, fats, antioxidants, amino acids, proteins, flavorings, coloring agents, hydrolyzed starch(es) and derivatives thereof or combinations thereof.

As used herein, the term "phospholipid" is recognized in the art, and refers to phosphatidyl glycerol, phosphatidyl inositol, phosphatidyl serine, phosphatidyl choline, phosphatidyl ethanolamine, as well as phosphatidic acids, ceramides, cerebrosides, sphingomyelins and cardiolipins.

As used herein, the term "antioxidant" is recognized in the art and refers to synthetic or natural substances that prevent or delay the oxidative deterioration of a compound. Exemplary antioxidants include tocopherols, flavonoids, catechins, superoxide dismutase, lecithin, gamma oryzanol; vitamins, such as vitamins A, C (ascorbic acid) and E and beta-carotene; natural components such as carnosol, carnosic acid and rosmanol found in rosemary and hawthorn extract, proanthocyanidins such as those found in grapeseed or pine bark extract, and green tea extract.

Additional flavonoids that can be incorporated into the soft gel capsule compositions of the invention include those plant pigments found in many foods that are thought to help protect the body from cancer. These include, for example, epi-gallo catechin gallate (EGCG), epi-gallo catechin (EGC) and epicatechin (EC).

Additional active ingredient(s) that can be included in the liquid formulation encapsulated within the soft gelatin capsule include cholesterol lowering drugs including, but not limited to, cholestyramine, colestipol, clofibrate, colesevelam (WelChol), gemfibrozil, niacin, fenofibrate (Tricor), Ezetimibe (Zetia), Lovastatin (Mevacor), Simvastatin (Zocor), Pravastatin (Pravachol), Fluvastatin (Lescol), Rosuvastatin Calcium (Crestor), Atorvastatin (Lipitor) or combinations thereof.

Other active ingredients(s) that can be included in the liquid formulation encapsulated within the soft gelatin capsule include those compounds that treat thrombosis and ischemic heart disease. These include, but are not limited to, aspirin (anti-platelet aggregating agents), beta-adrenergic blocking agents (e.g., propranonol, nadolol, timolol, etc.), nitrates (e.g., nitroglycerin) and calcium channel blockers (e.g., verapamil, nifedipine, diltiazem, etc and combination thereof.

Dosages for administration of naturally-occurring polymethoxyflavones range from about 1 to about 1000 mg/day, commonly from about 1 to about 500 mg/day, and typically from about 1 to about 100 mg/day. Generally, in terms of patient body weight, for about 70 kg body weight, usual dosages range from about 0.01 to about 15 mg/kg/day, commonly from about 0.01 to about 7.0 mg/kg/day, and typically from about 0.01 to about 2.0 mg/kg/day.

Dosages for administration of tocotrienols range from about 1 to about 1200 mg/day, commonly from about 1 to about 100 mg/day, and typically from about 1 to about 60 mg/day. Generally, in terms of patient body weight, usual dosages range from about 0.01 to about 20 mg/kg/day, commonly from about 0.01 to about 2.0 mg/kg/day, typically from about 0.01 to about 1.0 mg/kg/day.

Dosages for administration of limocitrin derivatives, quercetin derivatives, range from about 1 to about 1000 mg/day, commonly from about 1 to about 500 mg/day, and typically from about 1 to about 100 mg/day. Generally, in terms of patient body weight, for about 70 kg body weight, usual dosages range from about 0.01 to about 15 mg/kg/day, commonly from about 0.01 to about 7.0 mg/kg/day, and typically from about 0.01 to about 2.0 mg/kg/day.

Dosage amounts of active ingredients and intervals can be adjusted individually to provide plasma levels of the active ingredient(s) which are sufficient to maintain the cholesterol lowering or maintaining effects desired.

Soft gel or soft gelatin capsules can be prepared, for example, without limitation, by dispersing the liquid formulation in an appropriate vehicle (e.g. olive oil, rice bran oil, a monoterpene and/or beeswax) to form a high viscosity mixture. This mixture is then encapsulated with a gelatin based film using technology and machinery known to those in the soft gel industry. The industrial units so formed are then dried to constant weight. Typically, the weight of the capsule is between about 100 to about 2500 milligrams and in particular weigh between about 1500 and about 1900 milligrams, and more specifically can weigh between about 1500 and about 2000 milligrams. In particular, the soft gel capsule typically weighs between about 1000 milligrams and 1300 milligrams, wherein the percentage fill is about 50% of the entire weight of the capsule, i.e., from about 500 to about 650 milligrams fill weight. The fill weight includes the active ingredient(s), solubilizing agents, etc.

For example, when preparing soft gelatin shells, the shell can include between about 20 to 70 percent gelatin, generally a plasticizer and about 5 to about 60% by weight sorbitol. The filling of the soft gelatin capsule is liquid (principally rice bran oil and/or beeswax if desired) and can include, apart form the antioxidant actives, a hydrophilic matrix. The hydrophilic matrix, if present, is a polyethylene glycol having an average molecular weight of from about 200 to 1000. Further ingredients are optionally thickening agents. In one embodiment, the hydrophilic matrix includes polyethylene glycol having an average molecular weight of from about 200 to 1000, 5 to 15% glycerol, and 5 to 15% by weight of water. The polyethylene glycol can also be mixed with propylene glycol and/or propylene carbonate.

In another embodiment, the soft gel capsule is prepared from gelatin, glycerine, water and various additives. Typically, the percentage (by weight) of the gelatin is between about 30 and about 50 weight percent, in particular between about 35 and about weight percent and more specifically about 42 weight percent. The formulation includes between about 15 and about 25 weight percent glycerine, more particularly between about 17 and about 23 weight percent and more specifically about 20 weight percent glycerine.

The remaining portion of the capsule is typically water. The amount varies from between about 25 weigh percent and about 40 weight percent, more particularly between about 30 and about 35 weight percent, and more specifically about 35 weight percent. The remainder of the capsule can vary, generally, between about 2 and about 10 weight percent composed of a flavoring agent(s), sugar, coloring agent(s), etc. or combination thereof. After the capsule is processed, the water content of the final capsule is often between about 5 and about 10 weight percent, more particularly 7 and about 12 weight percent, and more specifically between about 9 and about 10 weight percent.

As for the manufacturing, it is contemplated that standard soft shell gelatin capsule manufacturing techniques can be used to prepare the soft-shell product. Examples of useful manufacturing techniques are the plate process, the rotary die process pioneered by R. P. Scherer, the process using the Norton capsule machine, and the Accogel machine and process developed by Lederle. Each of these processes are mature technologies and are all widely available to any one wishing to prepare soft gelatin capsules.

In one embodiment, the gelatin used to prepare the soft gelatin capsule includes gelatin from lime or acid derived gel manufacturing processes known in the art. The gelatin is combined with plasticizers, such as glycerin, sorbitol or other polyalcoholic compounds, or combinations thereof and purified water. Optional additives can include colorants, preservatives, flavors, sweetening agents and/or opacifying agents. The amount of gelatin in the mixture can range from about 30 to about 60 percent (by weight), with about 15 to about 55% plasticizer (by weight) and purified water from about 15 to about 40% by weight. Optional additives are generally present in a range from about 0.1 to about 15% by weight.

A soft gel capsule is prepared by mixing the active ingredient(s) and optional components with a suitable oil carrier or suspending agent, for a period of time until the mixture is thoroughly mixed, optionally under vacuum. A gelatin mixture is fed into two spreader boxes, which in turn form two gelatin ribbons that are used to make each half of the gelatin capsule shell. The fill mixture (active ingredient(s), olive oil, bees wax and limonene, as an example) is pumped into the gelatin ribbons held in place by two rotating die cavity rolls. The capsules are half sealed when a pump injects the fill material into the die cavities. The injection is followed by forming hermetic seals between the two capsule halves and the capsules are cut from the gelatin ribbon.

Typically, when a soft gel capsule is prepared, the total weight is between about 250 milligrams and about 2.5 gram in weight, e.g., 400-750 milligrams. Therefore, the total weight of additives, such as vitamins and antioxidants, is between about 80 milligrams and about 2000 milligrams, alternatively, between about 100 milligrams and about 1500 milligrams, and in particular between about 120 milligrams and about 1200 milligrams.

For example, a soft gel capsule can be prepared by mixing about 60 to about 75 grams of an active ingredient(s) with between about 200 grams and about 250 grams (e.g., 225 grams) olive oil, rice bran or soybean oil. The mixture can further include yellow bees wax and/or limonene. The mixture is then encapsulated within a gelatin capsule as described above.

The present invention also provides packaged formulations of a soft gel that contains a liquid solution of at least one PMF, and optionally, at least one tocotrienol, and instructions for use of the soft gel capsule. Typically, the packaged formulation, in whatever form, is administered to an individual in need thereof that requires an increase in the amount of the active ingredient(s) in the individual's diet. Typically, the dosage requirement is between about 1 to about 4 dosages a day.

As previously discussed, the soft gel compositions of the invention can treat or prevent one or more of the afflictions discussed throughout the present specification. As a consequence of these activities, the soft gel compositions of the invention can be used in a variety of in vitro, in vivo and ex vivo contexts to regulate or inhibit the afflictions described herein.

The soft gel compositions of the present invention can be administered to mammals for reduction, prevention, and treatment of cardiovascular diseases. Examples, not limited thereto, of cardiovascular diseases treatable by the soft gel compositions of the present invention include hypercholesterolemia, hyperlipidemia, atherosclerosis, thrombosis, myocardial infarction, etc.

When used to treat or prevent such diseases, the soft gelatin composition can be administered as mixtures of one or more active ingredients or in mixture or combination with other agents useful for treating such diseases and/or the symptoms associated with such diseases.

For oral administration, the compositions take the form of soft gel capsules prepared by conventional means described above that can include acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The soft gelatin capsules may be coated by methods well known in the art with, for example, sugars or enteric coatings.

The compositions can, if desired, be presented in a pack or dispenser device, which can contain one or more unit dosage forms containing the soft gel capsule with the encapsulated active ingredient(s). The pack can, for example, comprise metal or plastic foil, such as a blister pack. The pack or dispenser device can be accompanied by instructions for administration.

The nutraceutical compositions of the invention, will generally be used in an amount effective to achieve the intended result, for example in an amount effective to treat or prevent the particular affliction being treated. The nutraceutical can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the individual reports an improvement in feeling or condition, notwithstanding that the individual may still be afflicted with the underlying affliction. For example, administration of a nutraceutical to an individual suffering from increased levels of cholesterol provides therapeutic benefit not only when the underlying condition is eradicated or ameliorated, but also when the individual reports a decrease in cholesterol from the blood serum. Therapeutic benefit also includes halting or slowing the progression of the disease, regardless of whether improvement is realized.

For prophylactic administration, the soft gel compositions of the invention can be administered to an individual at risk of developing one of the previously described conditions. For example, if it is unknown whether an individual is likely to develop hypercholesterolemia, the nutraceutical can be taken to avoid or ameliorate hypercholesterolemia. Alternatively, prophylactic administration can be applied to avoid the onset of symptoms in an individual diagnosed with the underlying disorder.

The soft gel compositions that contain the active ingredients of the invention, e.g., PMF(s) and/or tocotrienol(s), can also be administered prophylactically to healthy individuals who are repeatedly exposed to high fat diets to prevent the onset of a cardiovascular disease.

The amount of active ingredient(s) administered will depend upon a variety of factors, including, for example, the particular indication being treated, whether the desired benefit is prophylactic or therapeutic, the severity of the indication being treated and the age and weight of the individual, etc. Determination of an effective dosage is well within the capabilities of those skilled in the art.

Effective dosages may be estimated initially from in vitro assays. For example, an initial dosage for use in animals may be formulated to achieve a circulating blood or serum concentration of active ingredient that is at or above an IC50 of the particular compound as measured in an in vitro assay. Calculating dosages to achieve such circulating blood or serum concentrations taking into account the bioavailability of the particular compound is well within the capabilities of skilled artisans. For guidance, the reader is referred to Fingl & Woodbury, "General Principles," In: Goodman and Gilman's The Pharmaceutical Basis of Therapeutics, Chapter 1, pp. 1-46, latest edition, Pagamonon Press, and the references cited therein.

Initial dosages can also be estimated from in vivo data, such as human or animal models. Animal models useful for testing the efficacy of compounds to treat or prevent the various diseases described above are well-known in the art. Suitable methods include those disclosed in U.S. Pat. No. 6,251,400 and U.S. Patent Publication No. 2004/0214882, the contents of which are incorporated herein by reference. Ordinarily skilled artisans can routinely adapt such information to determine dosages suitable for human administration.

The following examples are intended to be illustrative only and should not be considered limiting.

EXAMPLES

Formulations of Sytrinol™ can be prepared by the following ratios by mixing the components together and then encapsulating into a soft gel capsule.

| Component | Example 1 |
|---|---|
| Sytrinol ™ KGK Synergize (Canada) (consisting largely of tangeretin and nobiletin, 1:1, v/v, and palm oil tocotrienols) | 165 mg |
| Lecithin, NLT 62% Acetone Insolubles | 14 mg |
| Yellow Beeswax | 10 mg |
| Extra Virgin Olive Oil (cold pressed) | 241 mg |
| Gelatin (shell ingredient) | 166.68 mg |
| Glycerin (shell ingredient) | 78.73 mg |
| Purified Water (shell ingredient) | 26.15 mg |
| Orange Natural Flavor (limonene, shell ingredient) | 15.35 mg |
| Titanium Dioxide (shell ingredient) | 1.92 mg |
| Chlorophylline (shell ingredient) | 1.73 mg |
| Riboflavin based colorant (for imprint) | 0.001 mg |
| Net weight | 430 mg |
| Gross weight of capsule | 721 mg |

Each capsule provides approximately 81 mg of active PMF(s).

The resultant mixture of the above-identified components provides a fluid suspension that is encapsulated in soft gel capsules. The "fill weight" of 430 mg is encapsulated to afford a soft gel capsule having a total weight of between about 500 mg and 1000 mg, i.e., 721 mg, depending upon the die size used to prepare the soft gel capsule.

| Component | Example 2 |
|---|---|
| Sytrinol ™ KGK Synergize (Canada) (consisting largely of tangeretin and nobiletin, 1:1, v/v, and palm oil tocotrienols) | 165 mg |
| Marine Lipid Oil 150/100 mg EPA/DHA | 367.5 mg |
| Geraniol | 26.32 mg |
| Carmine Dispersion (shell ingredient) | 42.21 mg |
| Glycerin (shell ingredient) | 85.56 mg |
| Purified Water (shell ingredient) | 30.80 mg |
| Yellow Beeswax | 26 mg |
| Lecithin | 10.18 mg |
| Lemon Oil | 5 mg |
| Titanium Dioxide (shell ingredient) | 1.06 mg |
| Gelatin (shell ingredient) | 118.44 |
| Net weight | 600 mg |
| Gross weight of capsule | 943 mg |

| Component | Example 3 |
|---|---|
| Sytrinol ™ KGK Synergize (Canada) (consisting largely of tangeretin and nobiletin, 1:1, v/v, and palm oil tocotrienols) | 165 mg |
| Coenzyme Q-10 | 31.2 mg |
| Yellow Beeswax | 13.5 mg |
| Extra Virgin Olive Oil (cold pressed) | 325.27 mg |
| Gelatin (shell ingredient) | 195.20 mg |
| Glycerin (shell ingredient) | 78.28 mg |
| Purified Water (shell ingredient) | 28.40 mg |
| Annatto Extract (shell ingredient) | 15.91 mg |
| Titanium Dioxide (shell ingredient) | 0.195 mg |
| Net weight | 535 mg |
| Gross weight of capsule | 853 mg |

| Component | Example 4 |
|---|---|
| Sytrinol ™ KGK Synergize (Canada) (consisting largely of tangeretin and nobiletin, 1:1, v/v, and palm oil tocotrienols) | 165 mg |
| 150 mgEPA/'00 mg DHA ethyl esters | 250 mg |
| Yellow Beeswax | 11.5 mg |
| Extra Virgin Olive Oil (cold pressed) | 8.5 mg |
| Gelatin (shell ingredient) | 178.2 mg |
| Glycerin (shell ingredient) | 71.45 mg |
| Purified Water (shell ingredient) | 26.6 mg |
| Annatto Extract (shell ingredient) | 14.61 mg |
| Titanium Dioxide (shell ingredient) | 0.18 mg |
| Net weight | 435 mg |
| Gross weight of capsule | 726 mg |

| Component | Example 5 |
|---|---|
| Sytrinol ™ KGK Synergize (Canada) (consisting largely of tangeretin and nobiletin, 1:1, v/v, and palm oil tocotrienols) | 165 mg |
| Phytosterols (SterolSource TM), 95% Phytosterol | 105.3 mg |
| Yellow Beeswax | 15.0 mg |
| Extra Virgin Olive Oil (cold pressed) | 439.78 mg |
| Gelatin (shell ingredient) | 235.14 mg |
| Glycerin (shell ingredient) | 94.3 mg |
| Purified Water (shell ingredient) | 34.2 mg |
| Annatto (shell ingredient) | 19.17 mg |
| Titanium Dioxide (shell ingredient) | 0.24 mg |
| Net weight | 725 mg |
| Gross weight of capsule | 1,108 mg |

Preparation of the soft gel capsules was accomplished by methods well known in the art including, but not limited to, those described throughout the specification and in U.S. Pat. Nos. 6,616,942, 6,623,734 and pending U.S. Ser. Nos. 10/035,753 and 09/825,920, the contents of which are incorporated herein by reference in their entirety.

Data

The following experiments were undertaken to determine whether citrus polymethoxylated flavones (PMFs) can be detected and quantitated in serum obtained from healthy adults after a single-dose administration of Sytrinol™ capsules (containing 1053 mg of total PMFs) and to compare oral bioavailabilities of two Sytrinol™ formulations in healthy human subjects. This study was conducted as a randomized crossover trial in ten healthy adults, five men and five women, age 23±3 years. Participants were assigned to take a single dose of one of two Sytrinol™ products encoded as A or B (A: Sytrinol™ soft gel capsules; powdered B: Sytrinol™ in hard shell capsules) containing 1053 mg of PMFs, largely tangeretin and nobiletin, 1:1, v/v.

Peripheral blood was taken by venipuncture at time 0 (baseline) and times 0.25, 0.5, 1, 2, 4, 6, 8, 24 and 48 hours after ingestion of Sytrinol™ capsules. Serum was separated and aliquots were stored at −80° C. for analysis of free tangeretin and nobiletin. Citrus-free meals were provided during the day of multiple blood sampling. Participants took the second PMF product 14 days later. Blood samples were collected at the same time points. Tangeretin and nobiletin were detected in serum samples and quantitated by LC/MS/MS. The pharmacokinetic results demonstrated that for both tangeretin and nobiletin, the $AUC_{0-48h}$ and $C_{max}$ values were significantly higher after administration of formulation A than after treatment with formulation B, indicative of greater bioavailability of formulation A vs. B. The $T_{max}$ values were not affected by the type of treatment and also were similar for tangeretin and nobiletin peaks (1.3-1.4 h). For the two formulations, the $AUC_{0-48h}$ values were higher for nobiletin than for tangeretin indicating that nobiletin is more bioavailable than tangeretin.

Sytrinol™ is a proprietary cholesterol-lowering supplement developed by KGK Synergize Inc. Active components of Sytrinol™ include a group of citrus flavonoids called polymethoxylated flavones (PMFs), consisting largely of tangeretin and nobiletin, 1:1, v/v, and palm oil tocotrienols (a form of vitamin E).

The study was designed to determine whether PMFs can be detected and quantitated in serum obtained from healthy adults after a single dose administration of Sytrinol™ capsules (containing 1053 mg of total PMFs) and to compare oral bioavailabilies of two Sytrinol™ formulations in healthy human subjects.

The study was conducted as a randomized crossover trial. Ten healthy adults, five men and five women, age 23±3 years, were recruited for the study. Prior to the start of the study, subjects had blood drawn for routine tests to confirm eligibility. Those deemed eligible after the screening process were assigned blindly to one of two coded Sytrinol™ formulations. All subjects were asked to avoid caffeine-containing products 12 h prior to the study and during the study. Participants were asked to take a single dose of the first Sytrinol™ product (either Sytrinol™ soft gel capsules having the Sytrinol™ solvated in virgin olive oil, bees wax and limonene as described above in the EXAMPLE section or Sytrinol™ powder hard shell capsules, encoded as A or B) containing 1053 mg of PMFs, largely tangeretin and nobiletin, 1:1, v/v. Peripheral blood was taken by venipuncture at time 0 (baseline) and times 0.25, 0.5, 1, 2, 4, 6, 8, 24 and 48 hours after ingestion of Sytrino™ capsules. Serum was separated and aliquots (2×0.5 mL) were stored at −80° C. for determination of the main methoxylated flavones. Standard citrus-free meals (breakfast, lunch and dinner) were provided on each of the days of the multiple blood sampling. Participants took a second PMF dose 14 days later.

Quantitation of Tangeretin and Nobiletin in Serum by LC/MS/MS

A method of serum extraction and LC/MS/MS analysis of PMF was developed. A Varian 1200 L LC/MS/MS system equipped with ESI and APCI sources was used to identify and quantify tangeretin and nobiletin. The identity of these PMF was verified by comparing fragment ion mass spectra of authentic tangeretin and nobiletin standards.

Results

The baseline characteristic of the study subjects is summarized in FIG. 1. Tangeretin and nobiletin peaks were identified and quantitated in all serum samples collected after administration of Sytrinol™ formulations A or B. The pharmacokinetic evaluation of tangeretin and nobiletin for the two Sytrinol™ products is summarized in FIGS. 2 and 3. Changes in mean serum concentrations of tangeretin and nobiletin products after a single-dose administration of Sytrinol™ A or B formulations are shown in FIGS. 4 and 5. The effects of the Sytrinol™ formulations A and B on $AUC_{0-48h}$ and $C_{max}$ of tangeretin and nobiletin derivatives are depicted in FIGS. 6 and 7.

For both tangeretin and nobiletin, significantly higher $AUC_{0-48h}$ and $C_{max}$ values were obtained following the administration of formulation A, the soft gel capsule with an oil carrier than following the administration of formulation B having the dry powdered Sytrinol contained in a hard two piece gel capsule. The differences in $AUC_{0-48h}$ and $C_{max}$ values between A and B was more pronounced for nobiletin than for tangeretin (FIGS. 6 and 7). For nobiletin, the $AUC_{0-48h}$ values were 2.7-3.0 times higher for formulation A than for formulation B whereas for tangeretin, the $AUC_{0-48h}$ values were 1.7-2.3 times higher for formulation A than for formulation B.

The $T_{max}$ values were not significantly affected by the type of formulation. The $T_{max}$ was also similar for both PMFs (approximately 1.3 h and 1.4 h for tangeretin and nobiletin, respectively) (FIGS. 2 and 3).

For formulations A and B, the $AUC_{0-48h}$ values obtained for nobiletin were significantly higher than those obtained for tangeretin.

DISCUSSION AND CONCLUSIONS

The data demonstrates that serum samples obtained from healthy subjects following oral administration of two different Sytrinol™ formulations contained detectable amounts of tangeretin and nobiletin. These were quantitated in each treatment group and pharmacological evaluation was carried out to compare the bioavailability of the two Sytrinol™ formulations.

The time-concentration curves and pharmacokinetic results demonstrate that substantially higher $AUC_{0-48h}$ and $C_{max}$ values were obtained for both tangeretin and nobiletin following the administration of formula A having the oil carrier, bees wax and limonene as compared to dry powdered formulation B. The large differences in the $AUC_{0-48h}$ and $C_{max}$ between formulation A and formula B suggest that the bioavailability of Sytrinol™ formulation A was much greater then the bioavailabilities of Sytrinol™ formulation B.

For formulations A and B, the proportions of two the PMFs in blood serum differed from the proportions of tangeretin and nobiletin found in Sytrinol™. While in the capsules, both PMFs were present at equal amounts, more nobiletin than tangeretin was generally found in the blood. The differences were particularly striking in blood samples collected after administration of formulations A and B (with the $AUC_{0-48h}$ ratios of nobiletin to tangeretin 1.85 and 1.42, respectively). The results suggest that in healthy human subjects, nobiletin might be more bioavailable than tangeretin.

CONCLUSIONS

The pharmacokinetic results showed that in healthy human subjects, Sytrinol™ formulation A (Soft Gel PMF solvated with oil carrier) was significantly more bioavailable than formulation B (hard shell encasing dry powdered PMF). Formulation A differed from B in respect to $AUC_{0-48h}$ and $C_{max}$ but not in respect to $T_{max}$, which was not affected by treatments.

Although the present invention has been described with reference to preferred embodiments, persons skilled in the art will recognize that changes may be made in form and detail without departing from the spirit and scope of the invention.

All literature and patent references cited throughout the application are incorporated by reference into the application for all purposes.

What is claimed is:

1. A soft gelatin capsule for maintaining cardiovascular health comprising effective amounts of:
   nobiletin and tangeretin in about a 1:1, v:v ratio;
   tocotrienol, wherein the tocotrienol is derived from palm oil;
   at least one of a phytosterol, docosahexaenoic acid, Eicosapentanoic acid, coenzyme Q-10 or an analog thereof, polycosinol, red yeast rice, gugulipid, pantethine, garlic, chromium, carnitine, artichoke leaf, green tea, *Gym-* nema sylvestre, grape seed extract, pine bark extract, ginseng, silymarin or mixtures thereof; and an oil carrier.

2. The soft gelatin capsule of claim 1, wherein the tocotrienol is a mixture of tocotrienols.

3. The soft gelatin capsule of claim 1, wherein the oil carrier is olive or rice bran oil.

4. The soft gelatin capsule of claim 3, further comprising a monoterpene.

5. The soft gelatin capsule of claim 4, wherein the monoterpene is limonene.

6. The soft gelatin capsule of claim 4, further comprising titanium dioxide.

7. The soft gelatin capsule of claim 6, further comprising chlorophylline.

8. The soft gelatin capsule of claim 7, further comprising riboflavin.

9. The soft gelatin capsule of claim 2, wherein the oil carrier is olive or rice bran oil.

10. The soft gelatin capsule of claim 9, further comprising a monoterpene.

11. The soft gelatin capsule of claim 10, wherein the monoterpene is limonene.

12. The soft gelatin capsule of claim 10, further comprising titanium dioxide.

13. The soft gelatin capsule of claim 12, further comprising chlorophylline.

14. The soft gelatin capsule of claim 13, further comprising riboflavin.

15. The soft gelatin capsule of claim 1, further comprising cholestyramine, colestipol, clofibrate, colesevelam, gemfibrozil, niacin, fenofibrate, Ezetimibe, Lovastatin, Simvastatin, Pravastatin, Fluvastatin, Rosuvastatin Calcium, Atorvastatin or combinations thereof.

16. A packaged nutraceutical composition comprising the soft gelatin capsules according to claim 1.

17. A soft gelatin capsule comprising:
nobiletin and tangeretin in about a 1:1, v:v ratio;
a tocotrienol, wherein the tocotrienol is derived from palm oil;
at least one of a phytosterol, docosahexaenoic acid, Eicosapentanoic acid, coenzyme Q-10 or an analog thereof, polycosinol, red yeast rice, gugulipid, pantethine, garlic, chromium, carnitine, artichoke leaf, green tea, Gymnema sylvestre, grape seed extract, pine bark extract, ginseng, silymarin or mixtures thereof; and
an oil carrier;
wherein the capsule includes from about 5 to about 40 weight percent of the nobiletin and tangeretin and the tocotrienol.

18. The soft gelatin capsule of claim 17, wherein the capsule includes from about 10 to about 30 weight percent of the nobiletin and tangeretin and the tocotrienol.

* * * * *